(12) United States Patent
Warburton

(10) Patent No.: US 7,875,620 B2
(45) Date of Patent: Jan. 25, 2011

(54) METHODS OF TREATING MICROBIAL INFECTIONS

(75) Inventor: Mark J. Warburton, High Point, NC (US)

(73) Assignee: Piper Medical, Inc., High Point, NC (US)

( * ) Notice: Subject to any disclaimer, the term of this patent is extended or adjusted under 35 U.S.C. 154(b) by 1216 days.

(21) Appl. No.: 11/420,826

(22) Filed: May 30, 2006

(65) Prior Publication Data

US 2007/0003590 A1    Jan. 4, 2007

Related U.S. Application Data

(60) Provisional application No. 60/695,633, filed on Jun. 30, 2005.

(51) Int. Cl.
| | | |
|---|---|---|
| A01N 43/90 | (2006.01) | |
| A61K 31/522 | (2006.01) | |
| C07D 473/00 | (2006.01) | |

(52) U.S. Cl. .................. 514/263.33; 544/266
(58) Field of Classification Search ............ 514/263.33; 544/266
See application file for complete search history.

(56) References Cited

U.S. PATENT DOCUMENTS 5,994,306 A * 11/1999 Chang et al. .................. 514/13

FOREIGN PATENT DOCUMENTS

| JP | 47020349 | * 11/1974 |
|---|---|---|
| WO | WO 02/069949 | * 9/2002 |

OTHER PUBLICATIONS

Fan et. al., Bioorganic & Medicinal Chemistry Letters, Pergamon, vol. 7, pp. 3107-3112.*
Gold, The New England Journal of Medicine, Massachusetts Medical Society, vol. 335, pp. 1445-1453.*
Ruef, Infection, Urban & Vogel, vol. 6, pp. 315-327.*
Horl, American Journal of Nephrology, 1999, S Karger AG, vol. 19, No. 2, pp. 111-113.*

* cited by examiner

Primary Examiner—Sreeni Padmanabhan
Assistant Examiner—Sarah Pihonak
(74) Attorney, Agent, or Firm—Myers Bigel Sibley & Sajovec, PA

(57) ABSTRACT

The present invention provides methods of treating microbacterial infections comprising administering to a subject in need thereof, a composition comprising a compound of formula I:

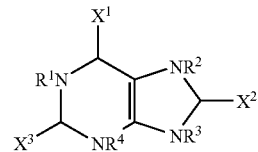

(I)

wherein:
$X^1$, $X^2$ and $X^3$ are selected from the group consisting of oxygen, sulfur, aminoalkyl, alkoxy, aryl, and heteroaryl, unsubstituted or substituted; and
$R^1$, $R^2$, $R^3$ and $R^4$ are selected from the group consisting of hydrogen, actinium, silicon, germanium, cyano, alkyl, alkoxy, allyl, alkenyl, alkynyl, alkylaryl, arylalkyl, aminoalkyl, alkylamino, alkene, alkyne, aryl, halide, alkylhalide, alkyloxyalkyl, thioalkyl, alkylthioalkyl, alkylamino, cycloalkyl, heterocyclyl, unsubstituted or substituted; or a pharmaceutically acceptable salt thereof. The present invention further provides methods of treating bacterial infections comprising administering to a subject in need thereof, an effective amount of a pharmaceutical composition comprising uric acid, urate, derivatives thereof, salts and hydrates thereof and prodrugs thereof and a pharmaceutically acceptable carrier.

7 Claims, No Drawings

METHODS OF TREATING MICROBIAL INFECTIONS

CROSS-REFERENCE TO RELATED APPLICATION

This application claims the benefit of U.S. Provisional Application No. 60/695,633, filed Jun. 30, 2005, the disclosure of which is incorporated by reference herein in its entirety.

FIELD OF THE INVENTION

The present invention concerns methods of reducing growth of microorganisms and treating microbial infections.

BACKGROUND OF THE INVENTION

Disease-causing microorganisms that have become resistant to drug therapy have increasingly become a public health concern. The mechanism of drug resistance varies with respect to the microorganism and the therapy employed (See generally, *Goodman & Gilman's, The Pharmacological Basis of Therapeutics* (9th ed. 1996)). For example, strains of *Staphylococcus aureus* exhibiting resistance to penicillin G appeared shortly after this antibiotic was introduced. The frequency of drug resistance has increased such that over 80% of both hospital- and community-acquired strains of *S. aureus* are now resistant. Other strains of *S. aureus* have emerged that are highly resistant to all beta-lactam antibiotics. These organisms, i.e., methicillin-resistant organisms, are prominent in hospitals, in particular, the intensive care unit where there is greater usage of antibiotics. Emergence of antimicrobial resistance has led to increasing challenges in treating illnesses such as tuberculosis, gonorrhea, malaria, and childhood ear infections. As a result of drug resistance to various microorganisms, diseases previously treatable by existing antibiotics may become untreatable, and there may be no adequate antibiotic treatment for newly discovered microbial-related illnesses.

In view of the foregoing, there is a need for new methods of eliminating, reducing or retarding the growth of microorganisms as well as new treatments for the diseases caused thereby.

SUMMARY OF THE INVENTION

The present invention relates to the antimicrobial properties of uric acid, urate, derivatives thereof, salts and hydrates thereof and prodrugs thereof.

In general, the present invention provides methods of treating microbial infections comprising administering to a subject in need thereof, a composition comprising a compound of formula I:

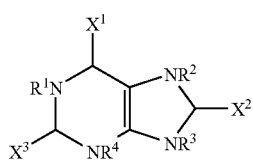

(I)

wherein:

$X^1$, $X^2$ and $X^3$ are selected from the group consisting of oxygen, sulfur, aminoalkyl, alkoxy, aryl, and heteroaryl, unsubstituted or substituted; and $R^1$, $R^2$, $R^3$ and $R^4$ are selected from the group consisting of hydrogen, actinium, silicon, germanium, cyano, alkyl, alkoxy, allyl, alkenyl, alkynyl, alkylaryl, arylalkyl, aminoalkyl, alkylamino, alkene, alkyne, aryl, halide, alkylhalide, alkyloxyalkyl, thioalkyl, alkylthioalkyl, alkylamino, cycloalkyl, heterocyclyl, unsubstituted or substituted; or a pharmaceutically acceptable salt thereof. In some aspects, the microbial infection is a bacterial infection.

Another aspect of the present invention provides a method of treating bacterial infections comprising administering to a subject in need thereof, an effective amount of a pharmaceutical composition comprising uric acid, urate, derivatives thereof, salts and hydrates thereof or prodrugs thereof and a pharmaceutically acceptable carrier.

A further aspect of the invention provides methods of eliminating, reducing or retarding the growth of a microorganism comprising contacting the microorganism with a compound of formula I. In some aspects, the microorganism causes a bacterial, mycobacterial, spirochetal, rickettsial, chlamydial, mycoplasmal, fungal, viral or parasitic infection.

A still further aspect of the invention provides use of a compound according to formula I in the preparation of a medicament for the treatment of microbial infections in a subject in need of such treatment.

Another aspect of the invention provides articles of manufacture comprising a composition comprising a compound of formula I for eliminating, reducing or retarding the growth of microorganisms and/or treatment of microbial infections.

A further aspect of the invention relates to the biocompatibility of the compound of formula I, compositions comprising the compound of formula I and substrates or articles of manufacture comprising the compound of formula I.

In some aspects of the invention, the compound of formula I is uric acid, urate or salts and hydrates or prodrugs thereof.

The foregoing and other aspects of the present invention are explained in greater detail in the specification set forth below.

DETAILED DESCRIPTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise. As used herein, the term "and/or" includes any and all combinations of one or more of the associated listed items.

All publications, patent applications, patents and other references cited herein are incorporated by reference in their entireties for the teachings relevant to the sentence and/or paragraph in which the reference is presented.

For purposes of this application, the chemical elements are identified in accordance with the Periodic Table of the Elements, CAS version, *Handbook of Chemistry and Physics*, 85th Ed., inside cover, and specific functional groups are defined as described therein. Additionally, general principles of organic chemistry, as well as specific functional moieties and reactivity, are described in *Organic Chemistry*, Francis A. Carey, McGraw-Hill, 2000, the contents of which are incorporated herein by reference.

1. Definitions

As used herein, the term "alkyl" refers to linear, branched, or cyclic, saturated or unsaturated (i.e., alkenyl and alkynyl) hydrocarbon chains, including for example, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The term "alkyl" specifically includes cycloalkyl hydrocarbon chains. "Lower alkyl" refers to C1 to C4 linear or branched alkyl, such as methyl, ethyl, propyl, butyl, isopropyl, sec-butyl, and tert-butyl. The term "alkyl" also encompasses substituted alkyls, which include aminoalkyls, hydroalkyls, oxygen-substituted alkyls (i.e., alkoxy groups), and halogen-substituted alkyls (i.e., alkyl halides, polyhaloalkyls) or other functionalities which have been suitably blocked with a protecting group so as to render the functionality non-interfering. "Aminoalkyl" refers to an amino group attached to the parent molecular moiety through an alkyl group. "Alkylamino" means an —$NH_2$ or —$NH_3^+$ group in which one or more of the hydrogen atoms on the nitrogen is replaced by an alkyl group. "Cycloalkyl" refers to saturated or partially unsaturated cyclic hydrocarbon groups having from 3 to 15 carbon atoms in the ring and to alkyl groups containing said cyclic hydrocarbon groups. Examples of cycloalkyls include, but are not limited to, cyclopropyl, cyclobutyl, cyclopentyl, and cyclohexyl. "Alkylaryl" refers to an alkyl-aryl-group in which the alkyl and aryl are described herein. Non-limiting examples of suitable alkylaryl groups include tolyl and xylyl. The alkylaryl is linked to an adjacent moiety through the aryl. "Arylalkyl" or "aralkyl" refer to an aryl-alkyl-group in which the aryl and alkyl are described herein. Non-limiting examples of suitable arylalkyl groups include benzyl, phenethyl and naphthalenylmethyl. The arylalkyl is linked to an adjacent moiety through the alkyl. "Thioalkyl" refers to an alkyl group attached to the parent molecular moiety through a sulfur atom. Examples of thioalkyl include, but are not limited to, methylthio, ethylthio, propylthio, isopropylthio, n-butylthio, and the like. "Alkoxy" refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like. "Alkenyl" refers to a hydrocarbon group, typically C2 to C4, derived from the corresponding alkyl and which contains at least one double bond (e.g., butadienyl). "Loweralkenyl" as used herein likewise refers to C1 to C4 alkenyl. "Alkynyl" refers to a hydrocarbon group, typically C2 to C4, derived from the corresponding alkyl and which contains at least one triple bond (e.g., butadiynyl).

As used herein, the term "aryl" refers to an aromatic group in a single or fused carbocyclic ring system having from 6 to 15 ring atoms, in some instances 6 to 10, and to alkyl groups containing aromatic groups. Examples of aryl groups include, but are not limited to, phenyl, 1-naphthyl, 2-naphthyl and benzyl.

As used herein, the term "heterocycle", "heterocyclic" or "heterocyclyl" refers to saturated or partially unsaturated monocyclic, bicyclic or tricyclic groups having from 3 to 15 atoms, in some instances 3 to 7, with at least one heteroatom in at least one of the rings. Heterocyclic also refers to alkyl groups containing said monocyclic, bicyclic or tricyclic heterocyclic groups.

As used herein, the term "hydroxy" refers to the group —OH.

As used herein, the term "carboxy" refers to the group —$CO_2H$.

As used herein, the term "carbonyl" refers to —C(O)—.

As used herein, the term "cyano" refers to the group —CN.

As used herein, the term "halo," "halogen" or "halide" refers to fluoro, fluorine or fluoride, chloro, chlorine or chloride, bromo, bromine or bromide, and iodo, iodine or iodide, accordingly.

Each substituent may be optionally substituted with additional non-interfering substituents. The term "non-interfering" characterizes the substituents as not adversely affecting the function of the compound to be performed in accordance with the methods described herein. The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by suitable substituents. The term "optionally substituted" is intended to expressly indicate that the specified group is unsubstituted or substituted by one or more suitable substituents such as specified groups, radicals or moieties, unless the substituents are expressly specified, in which case the term indicates that the group is unsubstituted or substituted with the specified substituents.

As used herein, the term "microbe" or "microorganism" refers to microscopic organisms that can exist as a single cell or cell clusters.

As used herein, the term "bacteriocidal" refers to killing the bacteria.

As used herein, the term "bacteriostatic" refers to inhibiting bacterial growth without killing.

As used herein, the term "eliminating" refers to complete cessation of the specified activity.

As used herein, the term "reducing" or "reduce" refers to a decrease or diminishment in the specified activity of at least about 10%, 25%, 35%, 40%, 50%, 60%, 75%, 80%, 90%, 95% or more. In some embodiments, the reduction results in little or essentially no detectable activity (at most, an insignificant amount, e.g., less than about 10% or even 5%).

As used herein, the term "retarding the growth" or "retardation of growth" refers to reducing, delaying and/or hindering activity contributing to the growth of the microorganism.

As used herein, the term "effective amount" refers to an amount of a compound or composition that is sufficient to produce the desired effect, which can be a therapeutic or agricultural effect. The effective amount will vary with the application for which the compound or composition is being employed, the microorganism and/or the age and physical condition of the subject, the severity of the condition, the duration of the treatment, the nature of any concurrent treatment, the pharmaceutically or agriculturally acceptable carrier used, and like factors within the knowledge and expertise of those skilled in the art. An appropriate "effective amount" in any individual case can be determined by one of ordinary skill in the art by reference to the pertinent texts and literature and/or by using routine experimentation. (See, for example for pharmaceutical applications, Remington, *The Science And Practice of Pharmacy* (9th Ed. 1995).

As used herein, the term "treat" refers to an action resulting in a reduction in the severity of the subject's condition or at least the condition is partially improved or ameliorated and/or that some alleviation, mitigation or decrease in at least one clinical symptom (or agricultural index for plants) is achieved and/or there is a delay in the progression of the condition and/or prevention or delay of the onset of the condition. Thus, the term "treat" refers to both prophylactic and therapeutic treatment regimes.

As used herein, the term "pharmaceutically acceptable carrier" refers to a component such as a carrier, diluent, or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects (such as toxicity, irritation, allergic response, death and the like). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents.

As used herein, the term "agriculturally acceptable carrier" refers to adjuvants, e.g., inert components, dispersants, surfactants, tackifiers, binders, etc. that are ordinarily used in agricultural formulation technology.

2. Active Agents

Active agents of the invention can include a compound of formula I:

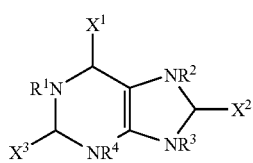

(I)

wherein:

$X^1$, $X^2$ and $X^3$ are selected from the group consisting of oxygen, sulfur, carbonyl, aminoalkyl, alkoxy, aryl, and heteroaryl, unsubstituted or substituted; and $R^1$, $R^2$, $R^3$ and $R^4$ are selected from the group consisting of hydrogen, actinium, silicon, germanium, cyano, alkyl, alkoxy, allyl, alkenyl, alkynyl, alkylaryl, arylalkyl, aminoalkyl, alkylamino, alkene, alkyne, aryl, halide, alkylhalide, alkyloxyalkyl, thioalkyl, alkylthioalkyl, alkylamino, cycloalkyl, heterocyclyl, unsubstituted or substituted;

or a pharmaceutically acceptable salt thereof.

In some embodiments, the compound of formula I is uric acid, urate, derivatives of uric acid or salts and hydrates thereof. In some embodiments, the compound of formula I can have the following structure:

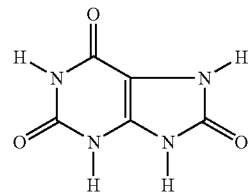

Salts of uric acid or urate include, but are not limited to sodium, calcium, potassium, ammonium or lithium. Examples of inorganic salts of uric acid include, but are not limited to sodium urate, potassium urate, calcium urate, sodium hydrogen urate, potassium hydrogen urate and calcium hydrogen urate. Examples of organic salts of uric acid include, but are not limited to, ammonium urate, ammonium hydrogen urate, and salts of uric acid with various amino acids. In some embodiments, the salt may include rubidium, copper, calcium, lanthanum, samarium, gadolimium, magnesium, neodymium, praseodymium, cerium, lutetium, ytterbium, thulium, erbium, holmium, dysprosium, terbium, nickel, iodide, cesium, zinc or lead. The salt forms can be mono-, di- or tri-salt forms. In some embodiments the salt compound is monosodium urate. The hydrate form of the compound can be a mono- or di-hydrate. In some embodiments, the compound can be monosodium urate monohydrate. Uric acid derivatives include, but are not limited to, alkyl modified uric acids (e.g., 3-N-methyl uric acid, 3-N-lauryl uric acid, 7-N-butyl uric acid, 1-N-ethyl uric acid, 9-N-lauryl uric acid, 3,7-N-dimethyl uric acid, etc.), uric acid glycosides (e.g., 3-N-ribosyl uric acid, 9-N-glycosyl uric acid, etc.). The compounds can be natural or synthetically produced.

Embodiments of the present invention further include prodrugs of the compounds of the present invention. The term "prodrug" refers to compounds that are rapidly transformed in vivo to yield the parent compound of the compounds according to embodiments of the present invention, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322. Additionally, the prodrugs of the present invention include pharmaceutically acceptable prodrugs (and like terms) of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

3. Microorganisms and Microbial Infections

Microorganisms that can be affected according to methods of the present invention include, but are not limited to, bacteria, mycobacteria, spirochetes, *rickettsia*, *chlamydia*, mycoplasma, fungi, viruses, and parasites. Accordingly, methods disclosed herein relate to bacterial, mycobacterial, spirochetal, rickettsial, chlamydial, mycoplasmal, fungal, viral, and parasitic infections.

In some embodiments, bacterial infections that can be treated using the active agents of the present invention can be caused by non-uric acid utilizing bacteria. For further description of uric acid utilizing bacteria, see U.S. Pat. No. 5,945,333 to Rehberger. Moreover, treatment of the bacterial infections described herein can be bacteriocidal or bacteriostatic.

Further bacterial infections that can be treated using the active agents of the present invention can be caused by bacteria such as gram-negative bacteria. Examples of gram-negative bacteria include, but are not limited to, bacteria of the genera *Salmonella, Escherichia, Klebsiella, Haemophilus, Pseudomonas, Proteus, Neisseria, Vibro, Helicobacter, Brucella, Bordetella, Legionella, Campylobacter, Francisella, Pasteurella, Yersinia, Bartonella, Bacteroides, Streptobacillus, Spirillum* and *Shigella*. Furthermore, bacterial infections that can be treated using the active agents of the present invention can be caused by gram-negative bacteria including, but not limited to, *Escherichia coli, Pseudomonas aeruginosa, Neisseria meningitides, Neisseria gonorrhoeae, Salmonella typhimurium, Salmonella entertidis, Klebsiella pneumoniae, Haemophilus influenzae, Haemophilus ducreyi, Proteus mirabilis, Vibro cholera, Helicobacter pylori, Brucella abortis, Brucella melitensis, Brucella suis, Bordetella pertussis, Bordetella parapertussis, Legionella pneumophila, Campylobacter fetus, Campylobacter jejuni, Francisella tularensis, Pasteurella multocida, Yersinia pestis, Bartonella bacilliformis, Bacteroides fragilis, Bartonella henselae, Streptobacillus moniliformis, Spirillum minus* and *Shigella dysenteriae*.

Bacterial infections that can be treated using the active agents of the present invention can also be caused by bacteria such as gram-positive bacteria. Examples of gram-positive bacteria include, but are not limited to, bacteria of the genera *Listeria, Staphylococcus, Streptococcus, Bacillus, Corynebacterium, Peptostreptococcus*, and *Clostridium*. Furthermore, bacterial infections that can be treated using the active agents of the present invention can be caused by gram-positive bacteria including, but not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae* and *Peptostreptococcus anaerobius*. In some embodiments, the gram-positive bacteria is methicillin-resistant *Staphylococcus aureus*.

Additional bacterial infections that can be treated using the active agents of the present invention can be caused by bacteria in the genera including, but not limited to, *Actinomyces, Propionibacterium, Nocardia* and *Streptomyces*. Furthermore, bacterial infections that can be treated using the active agents of the present invention can be caused by bacteria including, but not limited to, *Actinomyces israeli, Actinomyces gerencseriae, Actinomyces viscosus, Actinomyces naeslundii, Propionibacterium propionicus, Nocardia asteroides, Nocardia brasiliensis, Nocardia otitidiscaviarum* and *Streptomyces somaliensis*.

Mycobacterial infections that can be treated by the compounds of the present invention can be caused by mycobacteria belonging to the mycobacteria families including, but not limited to, Mycobacteriaceae. Additionally, mycobacterial infections that can be treated by the compounds of the present invention can be caused by mycobacteria including, but not limited to, *Mycobacterium tuberculosis, Mycobacterium leprae, Mycobacterium avium-intracellulare, Mycobacterium kansasii*, and *Mycobacterium ulcerans*.

Spirochetal infections that can be treated using the active agents of the present invention can be caused by spirochetes belonging to the genera including, but not limited to, *Treponema, Leptospira*, and *Borrelia*. Additionally, spirochetal infections that can be treated using the active agents of the present invention can be caused by the spirochetes including, but not limited to, *Treponema palladium, Treponema pertenue, Treponema carateum, Leptospira interrogans, Borrelia burgdorferi*, and *Borrelia recurrentis*.

Rickettsial infections that can be treated using the active agents of the present invention can be caused by *rickettsia* belonging to the genera including, but not limited to, *Rickettsia, Ehrlichia, Orienta, Bartonella* and *Coxiella*. Furthermore, rickettsial infections that can be treated using the active agents of the present invention can be caused by *rickettsia* including, but not limited to, *Rickettsia rickettsii, Rickettsia akari, Rickettsia prowazekii, Rickettsia typhi, Rickettsia conorni, Rickettsia sibirica, Rickettsia australis, Rickettsia japonica, Ehrlichia chaffeensis, Orienta tsutsugamushi, Bartonella quintana*, and *Coxiella burni*.

Chlamydial infections that can be treated using the active agents of the present invention can be caused by chlamydia belonging to the genera including, but not limited to, *Chlamydia*. Furthermore, chlamydial infections that can be treated using the active agents of the present invention can be caused by chlamydia including, but not limited to, *Chlamydia trachomatis, Chlamydia caviae, Chlamydia pneumoniae, Chlamydia muridarum, Chlamydia psittaci*, and *Chlamydia pecorum*.

Mycoplasmal infections that can be treated using the active agents of the present invention can be caused by mycoplasma belonging to the genera including, but not limited to, *Mycoplasma* and *Ureaplasma*. In addition, mycoplasmal infections that can be treated using the active agents of the present invention can be caused by mycoplasma including, but not limited to, *Mycoplasma pneumoniae, Mycoplasma hominis, Mycoplasma genitalium*, and *Ureaplasma urealyticum*.

Fungal infections that can be treated using the active agents of the present invention can be caused by fungi belonging to the genera including, but not limited to, *Aspergillus, Candida, Cryptococcus, Coccidioides, Tinea, Sporothrix, Blastomyces, Histoplasma*, and *Pneumocystis*. Additionally, fungal infections that can be treated using the active agents of the present invention can be caused by fungi including, but not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum*, and *Histoplasma duboisii*.

Viral infections that can be treated using the active agents of the present invention can be caused by viruses belonging to the viral families including, but not limited to, Flaviviridae, Arenaviradae, Bunyaviridae, Filoviridae, Poxyiridae, Togaviridae, Paramyxoviridae, Herpesviridae, Picornaviridae, Caliciviridae, Reoviridae, Rhabdoviridae, Papovaviridae, Parvoviridae, Adenoviridae, Hepadnaviridae, Coronaviridae, Retroviridae, and Orthomyxoviridae. Furthermore, viral infections that can be treated using the active agents of the present invention can be caused by the viruses including, but not limited to, Yellow fever virus, St. Louis encephalitis virus, Dengue virus, Hepatitis G virus, Hepatitis C virus, Bovine diarrhea virus, West Nile virus, Japanese B encephalitis virus, Murray Valley encephalitis virus, Central European tick-borne encephalitis virus, Far eastern tick-born encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Lymphocytic choriomeningitis virus, Junin virus, Bolivian hemorrhagic fever virus, Lassa fever virus, California encephalitis virus, Hantaan virus, Nairobi sheep disease virus, Bunyamwera virus, Sandfly fever virus, Rift valley fever virus, Crimean-Congo hemorrhagic fever virus, Marburg virus, Ebola virus, Variola virus, Monkeypox virus, Vaccinia virus, Cowpox virus, Orf virus, Pseudocowpox virus, Molluscum contagiosum virus, Yaba monkey tumor virus, Tanapox virus, Raccoonpox virus, Camelpox virus, Mousepox virus, Tanterapox virus, Volepox virus, Buffalopox virus, Rabbitpox virus, Uasin gishu disease virus, Sealpox virus, Bovine papular stomatitis virus, Camel contagious eethyma virus, Chamios contagious eethyma virus, Red squirrel parapox virus, Juncopox virus, Pigeonpox virus, Psittacinepox virus, Quailpox virus, Sparrowpox virus, Starlingpox virus, Peacockpox virus, Penguinpox virus, Mynahpox virus, Sheeppox virus, Goatpox virus, Lumpy skin disease virus, Myxoma virus, Hare fibroma virus, Fibroma virus, Squirrel fibroma virus, Malignant rabbit fibroma virus, Swinepox virus, Yaba-like disease virus, Albatrosspox virus, Cotia virus, Embu virus, Marmosetpox virus, Marsupialpox virus, Mule deer poxvirus virus, Volepox virus, Skunkpox virus, Rubella virus, Eastern equine encephalitis virus, Western equine encephalitis virus, Venezuelan equine encephalitis virus, Sindbis virus, Semliki forest virus, Chikungunya virus, O'nyong-nyong virus, Ross river virus, Parainfluenza virus, Mumps virus, Measles virus (rubeola virus), Respiratory syncytial virus, Herpes simplex virus type 1, Herpes simplex virus type 2, *Varicella*-zoster virus, Epstein-Barr virus, Cytomegalovirus, Human b-lymphotrophic virus, Human herpesvirus 7, Human herpesvirus 8, Poliovirus, Coxsackie A virus, Coxsackie B virus, ECHO-virus, Rhinovirus, Hepatitis A virus, Mengovirus, ME virus, Encephalomyocarditis (EMC) virus, MM virus, Columbia SK virus, Norwalk agent, Hepatitis E virus, Colorado tick fever virus, Rotavirus, Vesicular stomatitis virus, Rabies virus, Papilloma virus, BK virus, JC virus, B19 virus, Adeno-associated virus, Adenovirus (including serotypes 3, 7, 14, 21), Hepatitis B virus, Coronavirus, Human T-cell lymphotrophic virus, Human immunodeficiency virus, Human foamy virus, Influenza viruses, types A, B, C, and Thogotovirus.

Plant viruses include viruses in the following groups: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites.

Geminiviruses encompass viruses of the Genus Mastrevirus, Genus Curtovirus, and Genus Begomovirus. Exemplary geminiviruses include, but are not limited to, Abutilon Mosaic Virus, Ageratum Yellow Vein Virus, Bhendi Yellow Vein Mosaic virus, Cassaya African Mosaic Virus, Chino del Tomato Virus, Cotton Leaf Crumple Virus, Croton Yellow Vein Mosaic Virus, Dolichos Yellow Mosaic Virus, Horsegram Yellow Mosaic Virus, Jatropha Mosaic virus, Lima Bean Golden Mosaic Virus, Melon Leaf Curl Virus, Mung Bean Yellow Mosaic Virus, Okra Leaf Curl Virus, Pepper Hausteco Virus, Potato Yellow Mosaic Virus, Rhynchosia Mosaic Virus, Squash Leaf Curl Virus, Tobacco Leaf Curl Virus, Tomato Australian Leaf Curl Virus, Tomato Indian Leaf Curl Virus, Tomato Leaf Crumple Virus, Tomato Yellow Leaf Curl Virus, Tomato Yellow Mosaic Virus, Watermelon Chlorotic Stunt Virus, Watermelon Curly Mottle Virus, Bean Distortion Dwarf Virus, Cowpea Golden Mosaic Virus, Lupin Leaf Curl Virus, Solanum Apical Leaf Curling Virus, Soybean Crinkle Leaf Virus, Chloris Striate Mosaic Virus, Digitaria Striate Mosaic Virus, Digitaria Streak Virus, Miscanthus Streak Virus, Panicum Streak Virus, Pasalum Striate Mosaic Virus, Sugarcane Streak Virus, Tobacco Yellow Dwarf Virus, Cassaya Indian Mosaic Virus, Serrano Golden Mosaic Virus, Tomato Golden Mosaic Virus, Cabbage Leaf Curl Virus, Bean Golden Mosaic Virus, Pepper Texas Virus, Tomato Mottle Virus, Euphorbia Mosaic Virus, African Cassaya Mosaic Virus, Bean Calico Mosaic Virus, Wheat Dwarf Virus, Cotton Leaf Curl Virus, Maize Streak Virus, and any other virus designated as a Geminivirus by the International Committee on Taxonomy of Viruses (ICTV).

Badnaviruses are a genus of plant viruses having double-stranded DNA genomes. Specific badnavirus include cacao swollen shoot virus and rice tungro bacilliform virus (RTBV). Most badnavirus have a narrow host range and are transmitted by insect vectors. In the badnaviruses, a single open reading frame (ORF) may encode the movement protein, coat protein, protease and reverse transcriptase; proteolytic processing produces the final products.

Exemplary Badnaviruses include, but are not limited to Commelina Yellow Mottle Virus, Banana Streak Virus, Cacao Swollen Shoot Virus, Canna Yellow Mottle Virus, Dioscorea Bacilliform Virus, Kalanchoe Top-Spotting Virus, Piper Yellow Mottle Virus, Rice Tungro Bacilliform Virus, Schefflera Ringspot Virus, Sugarcane Bacilliform Virus, Aucuba Bacilliform Virus, Mimosa Baciliform Virus, Taro Bacilliform Virus, Yucca Bacilliform Virus, Rubus Yellow Net Virus, Sweet Potato Leaf Curl Virus, Yam Internal Brown Spot Virus, and any other virus designated as a Badnavirus by the International Committee on Taxonomy of Viruses (ICTV).

Caulimoviruses have double-stranded circular DNA genomes that replicate through a reverse transcriptase-mediated process, although the virus DNA is not integrated into the host genome. As used herein, Caulimoviruses include but are not limited to Cauliflower Mosaic Virus, Blueberry Red Ringspot Virus, Carnation Etched Ring Virus, Dahlia Mosaic Virus, Figwort Mosaic Virus, Horseradish Latent Virus, Mirabilis Mosaic Virus, Peanut Chlorotic Streak Virus, Soybean Chlorotic Mottle Virus, Strawberry Vein Banding Virus, Thistle Mottle Virus, Aquilegia Necrotic Mosaic Virus, Cestrum Virus, Petunia Vein Clearing Virus, Plantago Virus, Sonchus Mottle Virus, and any other virus designated as a Caulimovirus by the International Committee on Taxonomy of Viruses (ICTV).

The Nanoviruses have single-stranded circular DNA genomes. As used herein, Nanoviruses include but are not limited to Banana Bunchy Top Nanavirus, Coconut Foliar Decay Nanavirus, Faba Bean Necrotic Yellows Nanavirus, Milk Vetch Dwarf Nanavirus, and any other virus designated as a Nanovirus by the International Committee on Taxonomy of Viruses (ICTV).

Parasitic infections that can be treated using the active agents of the present invention can be caused by parasites belonging to the genera including, but not limited to, *Entamoeba, Dientamoeba, Giardia, Balantidium, Trichomonas, Cryptosporidium, Isospora, Plasmodium, Leishmania, Trypanosoma, Babesia, Naegleria, Acanthamoeba, Balamuthia, Enterobius, Strongyloides, Ascaradia, Trichuris, Necator, Ancylostoma, Uncinaria, Onchocerca, Mesocestoides, Echinococcus, Taenia, Diphylobothrium, Hymenolepsis, Moniezia, Dicytocaulus, Dirofilaria, Wuchereria, Brugia, Toxocara, Rhabditida, Spirurida, Dicrocoelium, Clonorchis, Echinostoma, Fasciola, Fascioloides, Opisthorchis, Paragonimus*, and *Schistosoma*. Additionally, parasitic infections that can be treated using the active agents of the present invention can be caused by parasites including, but not limited to, *Entamoeba histolytica, Dientamoeba fragilis, Giardia lamblia, Balantidium coli, Trichomonas vaginalis, Cryptosporidium parvum, Isospora belli, Plasmodium malariae, Plasmodium ovale, Plasmodium falciparum, Plasmodium vivax, Leishmania braziliensis, Leishmania donovani, Leishmania tropica, Trypanosoma cruzi, Trypanosoma brucei, Babesia divergens, Babesia microti, Naegleria fowleri, Acanthamoeba culbertsoni, Acanthamoeba polyphaga, Acanthamoeba castellanii, Acanthamoeba astronyxis, Acanthamoeba hatchetti, Acanthamoeba rhysodes, Balamuthia mandrillaris, Enterobius vermicularis, Strongyloides stercoralis, Strongyloides fuilleborni, Ascaris lumbricoides, Trichuris trichiura, Necator americanus, Ancylostoma duodenale, Ancylostoma ceylanicum, Ancylostoma braziliense, Ancylostoma caninum, Uncinaria stenocephala, Onchocerca volvulus, Mesocestoides variabilis, Echinococcus granulosus, Taenia solium, Diphylobothrium latum, Hymenolepis nana, Hymenolepis diminuta, Moniezia expansa, Moniezia benedeni, Dicytocaulus viviparous, Dicytocaulus filarial, Dicytocaulus arnfieldi, Dirofilaria repens, Dirofilaria immitis, Wuchereria bancrofti, Brugia malayi, Toxocara canis, Toxocara cati, Dicrocoelium dendriticum, Clonorchis sinensis, Echinostoma, Echinostoma ilocanum, Echinostoma jassyenese, Echinostoma malayanum, Echinostoma caproni, Fasciola hepatica, Fasciola gigantica, Fascioloides magna, Opisthorchis viverrini, Opisthorchis felineus, Opisthorchis sinensis, Paragonimus westermani, Schistosoma japonicum, Schistosoma mansoni, Schistosoma haematobium* and *Schistosoma haematobium*.

4. Pharmaceutical Formulations

The active agents of the present invention can be prepared in the form of their pharmaceutically acceptable salts. As understood by one of skill in the art, pharmaceutically acceptable salts are salts that retain the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine; and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The active agents can be formulated for administration in accordance with known pharmacy techniques. See, e.g., Remington, *The Science And Practice of Pharmacy* ($9^{th}$ Ed. 1995). In the manufacture of a pharmaceutical composition according to the present invention, the active agents (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier can be a solid or a liquid, or both, and can be formulated with the active agent as a unit-dose formulation, for example, a tablet, which can contain from 0.01% or 0.5% to 95% or 99%, or any value between 0.01% and 99%, by weight of the active agent. One or more active agents can be incorporated in the compositions of the invention, which can be prepared by any of the well-known techniques of pharmacy, comprising admixing the components, optionally including one or more accessory ingredients. Moreover, the carrier can be preservative free, as described herein above.

In some embodiments, the active agents comprise a lower limit ranging from about 0.01, 0.02, 0.03, 0.04, 0.05, 0.06, 0.07, 0.08, 0.09, 1, 2, 3, 4, 5, 6, 7, 8, 9, and 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by weight of the composition. In some embodiments, the active agent includes from about 0.05% to about greater than 99% by weight of the composition.

The pharmaceutical compositions according to embodiments of the present invention include those suitable for oral, rectal, topical, inhalational (e.g., via an aerosol) buccal (e.g., sub-lingual), vaginal, topical (i.e., skin, ocular and mucosal surfaces, including airway surfaces), intraoperative, transdermal administration and parenteral (e.g., subcutaneous, intramuscular, intradermal, intraarticular, intrapleural, intraperitoneal, intraarterial, or intravenous), although the most suitable route in any given case will depend on the nature and severity of the condition being treated and on the nature of the particular active agent which is being used.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes bringing into association the active compound and a suitable carrier (which can contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granules containing the active compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations of the present invention suitable for parenteral administration comprise sterile aqueous and non-aqueous injection solutions of the active compound, which preparations are preferably isotonic with the blood of the intended recipient. These preparations can contain buffers and solutes that render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described.

For example, in one aspect of the present invention, there is provided an injectable, stable, sterile composition comprising active compounds, or a salt thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable can be employed in sufficient quantity to emulsify the compound or salt in an aqueous carrier. Non-limiting examples of agents that contribute to the pharmaceutical acceptability of the compositions of the present invention include normal saline, phosphatidyl choline, and glucose. In some embodiments, the pharmaceutically acceptable carrier can be normal saline. In other embodiments, the pharmaceutically acceptable carrier can be normal saline with up to 0.0, 0.01, 0.02, 0.03, 0.04, 0.05, 0.06, 0.07, 0.08, 0.09, 1, 2, 3, 4, 5, 6, 7, 8, 9, 10, 11, 12, 13, 14, 15, 16, 17, 18, 19, and 20%, and any value between 0.01% and 20%, glucose.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3(6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

The compounds and compositions of the present invention can be administered by any means that transports the active agents to the lung including, but not limited to, nasal administration, inhalation, and insufflation. The active agents disclosed herein can be administered to the lungs of a patient by any suitable means, but are preferably administered by generating an aerosol comprised of respirable particles, the respirable particles comprised of the active agents, which particles the subject inhales. The respirable particles can be liquid or solid, and they can optionally contain other therapeutic ingredients, including, but not limited to surfactants.

Particles comprised of active agents for practicing the present invention should be administered as a formulation including particles of respirable size: that is, particles of a size sufficiently small to pass through the nose, mouth and larynx upon inhalation and into the bronchi and alveoli of the lungs. In general, respirable particles range from about 0.5 to 10 microns in diameter. Particles of non-respirable size that are included in the aerosol tend to deposit in the throat and be swallowed. Accordingly, the quantity of non-respirable particles in the aerosol is preferably minimized. For nasal administration, a particle size in the range of 10-500 µm is preferred to ensure retention in the nasal cavity. Alternatively, droplets can be given.

Liquid pharmaceutical compositions of active agents for producing an aerosol can be prepared by combining the active agents with a suitable vehicle, such as sterile pyrogen free water. Other therapeutic compounds can optionally be included. The aerosols of liquid particles comprising the active agents can be produced by any suitable means, such as with a nebulizer. See e.g., U.S. Pat. No. 4,501,729.

Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w, but preferably less than 20% w/w, of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

The aerosols of solid particles comprising the active agents can likewise be produced with any solid particulate medicament aerosol generator. Aerosol generators for administering solid particulate medicaments to a subject produce particles, which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders that can be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, surfactants, such as oleic acid or sorbitan trioleate, antioxidants and suitable flavoring agents.

The aerosol, whether formed from solid or liquid particles, can be produced by the aerosol generator at a rate of from about 10 to 150 liters per minute, more preferably from about 30 to 150 liters per minute, and most preferably about 60 liters per minute. Aerosols containing greater amounts of medicament can be administered more rapidly.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants.

Formulations suitable for topical administration include those for medical use and use in personal care and/or hygiene (e.g., soaps, skin creams, soaps, cleansers, shampoos). Topical compositions can include the active agents with vitamin E, vitamin A, conjugated linoleic acid, and essential fatty acids. The topical compositions disclosed herein are suitable for topical application to mammalian skin. The compositions comprise a safe and effective amount of the active agents, and a cosmetically and/or pharmaceutically acceptable topical carrier. The phrase "cosmetically acceptable carrier", as used herein, means any substantially non-toxic carrier suitable for topical administration to the skin, which has good aesthetic properties, and is compatible with the active agent of the present invention. By "compatible" it is meant that the active agent will remain stable and retain substantial activity therein. The carrier can be in a wide variety of forms, such as sprays, emulsions, mousses, liquids, creams, oils, lotions, ointments, gels and solids.

Suitable pharmaceutically acceptable topical carriers include, but are not limited to, water, glycerol, alcohol, propylene glycol, fatty alcohols, triglycerides, fatty acid esters, and mineral oils. Suitable topical cosmetically acceptable carriers include, but are not limited to, water, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically and/or cosmetically-acceptable carrier is substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

For intraoperative administration, compounds of formula I can be mixed in a solution and applied, for example, as a wash. The compounds and/or solution comprising the same can be mixed with a polymer. The polymer may harden and be shaped as a space occupying antimicrobial bead. An exemplary polymer is polymethyl methacrylate (PMM).

Further, the present invention provides liposomal formulations of the active agents including salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations including the active agents and salts thereof, can be lyophilized to produce a lyophilizate which can be reconstituted with a pharmaceutically acceptable carrier, such as water, to regenerate a liposomal suspension.

Other pharmaceutical compositions can be prepared from the active agents in view of the relative water-insolubility of the some of the active agents, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

Formulations of the present invention further include sustained release preparations. Sustained preparations can be formulated according to methods as understood by one skilled in the art. For example, the compounds of formula I can be mixed with commercially available preparations such a calcium sulphate and calcium phosphate preparations, which are slowly reabsorbed by the body releasing the active agent. Moreover, the compounds of formula I may be bound to an ion exchange resin which is optionally coated with a diffusion barrier to modify the release properties of the resin to enable controlled release of the active agent.

In addition to active agents or their salts, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. The pharmaceutical compositions of the present invention can be lyophilized using techniques well known in the art.

5. Methods of Use

Embodiments according to the present invention relate to methods of treating microbial infections comprising administering to a subject in need thereof, a composition comprising a compound of formula I. According to embodiments of the invention, microbial infections treated according to the methods disclosed herein include bacterial, mycobacterial, spirochetal, rickettsial, chlamydial, mycoplasmal, fungal, viral, and parasitic infections. In particular, uric acid, urate, derivatives thereof and salts and hydrates thereof can be utilized to kill and/or inhibit the proliferation and/or growth of microorganisms described herein. The invention further provides methods of eliminating, reducing or retarding the growth of a microorganism described herein comprising contacting the microorganism with a compound of formula I. In some embodiments, the method includes contacting a surface suspected of having a microorganism thereon. In other embodiments, the method includes contacting the microorganism with a compound of formula I in vivo. In still other embodiments, the method includes contacting the microorganism with a compound of formula I in vitro. In some embodiments, the microbial infection is a bacterial infection. In particular embodiments, the microbial infection is methicillin-resistant *Staphylococcus aureus*. In some embodiments, the microbial infection can be caused by multiple types of microorganisms.

In some embodiments, contacting the microorganism with a compound of formula I can be used for treatment purposes. In other embodiments, the compound of formula I can be used for cleaning surfaces or as an antiseptic or disinfectant. In still other embodiments, contacting the microorganism with a compound of formula I can be used for screening or diagnostic purposes, for example, to identify a likely antimicrobial therapy prior to administration to the subject.

Methods of the invention further include treating bacterial infections comprising administering to a subject in need thereof, an effective amount of a pharmaceutical composition comprising uric acid, urate, derivatives thereof, salts and hydrates thereof or prodrugs thereof and a pharmaceutically acceptable carrier. As noted above in Section I, the effective amount of the composition will vary somewhat from subject to subject, and will depend upon factors such as the age and condition of the subject and the route of delivery. Such dosages can be determined in accordance with routine pharmacological procedures known to those skilled in the art. For example, the active agents of the present invention can be administered to the subject in an amount ranging from a lower limit of about 0.01, 0.02, 0.03, 0.04, 0.05, 0.06, 0.07, 0.08, 0.09, or 0.1 mg to an upper limit of about 0.1, 0.2, 0.3, 0.4, 0.5, 0.6, 0.7, 0.8, 0.9, 1, 2, 3, 4, 5, 6, 7, 8, 9, or 10 mg in a single dose; in an amount ranging from a lower limit of about 0.01, 0.02, 0.03, 0.04, 0.05, 0.06, 0.07, 0.08, 0.09, or 0.1 mg to an upper limit of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or 20 mg in a 24 hour period. In some embodiments, the dosage can be in a range from about 0.1 mg/kg to about 100 mg/kg of total body weight of said individual. The frequency of administration can be one, two, three, four, five times or more per day or as necessary to control the condition. The duration of therapy depends on the type of condition being treated and can be for as long as the life of the subject.

The present invention further provides use of a compound according to formula I in the preparation of a medicament for the treatment of microbial infections as described herein in a subject in need of such treatment, by administering to the subject an effective amount of the compound according to formula I. In some embodiments, use of the compound in the preparation of a medicament includes the use of uric acid, urate, derivatives thereof, salts and hydrates thereof or prodrugs thereof.

Embodiments of the invention further provide articles of manufacture comprising the active agents described herein and methods of making the articles. In particular, the active agents applied to the article of manufacture can be formulated or unformulated. Articles of manufacture as used herein relate to products capable of being worn or applied for the purpose of providing access to or contact with the site of infection. Such articles include, but are not limited to, socks, gloves, shoes, hats, shoe inserts, masks, bandages, gauze, dressings, and the like. According to embodiments of the present invention, active agents can be applied to or formulated with the substrate by means known to those of ordinary skill in the art. For example, the active agents can be applied to the substrate by spraying, coating, dipping, etc. Substrates as used herein relate to objects upon which the active agents can be applied or become integrated. In some embodiments, suitable substrates include articles of manufacture as listed above and orthopedic implants.

In particular embodiments, the active agents can be incorporated into soaps, wipes, cosmetics, lotions, creams, gels, sprays, ointments, rinses, hydrocolloids and dressings (e.g., bandages) for long term and short term use.

The invention further provides methods of eliminating, reducing or retarding the growth of microbes affecting plants. The method includes contacting a plant structure, i.e., a part of the plant or the entire plant, with a compound or composition comprising the active agents. Contacting the plant can include direct contact, for example, application directly onto the plant, such as spraying the plant. Contacting the plant can further include indirect contact, for example, application by way of a plant's root system through a medium, such as during the process of providing nourishment to the plant. The composition can include agriculturally acceptable carriers.

Subjects suitable to be treated according to the present invention include, but are not limited to, avian, mammalian and plant subjects. Illustrative avians according to the present invention include chickens, ducks, turkeys, geese, quail, pheasant, ratites (e.g., ostrich) and domesticated birds (e.g., parrots and canaries), and birds in ovo.

Mammals of the present invention include, but are not limited to, canines, felines, bovines, caprines, equines, ovines, porcines, rodents (e.g. rats and mice), lagomorphs, primates (including non-human primates), humans, and the like, and mammals in utero. Any mammalian subject in need of being treated according to the present invention is suitable. According to some embodiments of the present invention, the mammal is a non-human mammal. In some embodiments, the mammal is a human subject. Human subjects of both genders and at any stage of development (i.e., neonate, infant, juvenile, adolescent, adult) can be treated according to the present invention.

Plants according to the present invention include seeds, seedlings, bushes, trees and cut flowers. Plants include, but are not limited to, corn (*Zea mays*), canola (*Brassica napus, Brassica rapa* ssp.), alfalfa (*Medicago saliva*), rice (*Oryza sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotian a tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*). duckweed (*Lemna*), oats, barley, vegetables, ornamentals, conifers, and turfgrasses (e.g., for ornamental, recreational or forage purposes).

Vegetables include *Solanaceous* species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana,* and *C. martinezii*, and members of the genus *Cucumis* such as cucumber (*Cucumis sativus*), cantaloupe (*C. cantalupensis*), and musk melon (*C. melo*).

Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*dianthus caryophyllus*), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrasses include, but are not limited to zoysia grasses, bent grasses, fescue grasses, blue grasses, St. Augustine grasses, Bermuda grasses, buffalograsses, rye grasses and orchard grasses.

The present invention is concerned with the treatment of human subjects, but the invention can also be carried out on animal subjects, particularly mammalian subjects such as mice, rats, dogs, cats, livestock and horses for veterinary purposes, and for drug screening and drug development purposes.

The present invention will now be described with reference to the following example. It should be appreciated that this example is for the purpose of illustrating aspects of the present invention, and does not limit the scope of the invention as defined by the claims.

EXAMPLE

Antimicrobial Activity of Monosodium Urate Monohydrate

A chalky, white substance presumptively identified as monosodium urate monohydrate crystals was extracted from the subcutaneous area of an elbow of a patient presenting with a soft tissue gouty tophus at the elbow. Under polarized light, the crystalline material showed the birefringence characteristic of urate crystals. The crystalline substance was swabbed onto agar plates containing *Staphylococcus aureus, Staphylococcus pyogenes, Neisseria meningitis, Neisseria gonorrhorea, Escherichia coli*, Methicillin resistant *Staphylococcus aureus, Haemophilus influenza* or *Serratia Marcessens*. The crystalline material inhibited the growth of the microorganisms as indicated below in Table 1.

TABLE 1

| Antimicrobial Activity of Monosodium Urate Monohydrate | |
|---|---|
| Inhibited growth | Did not inhibit growth |
| *Staphylococcus aureus* | *Escherichia coli* |
| *Staphylococcus pyogenes* | Methicillin resistant *Staphylococcus aureus* |
| *Neisseria meningitis* | *Haemophilus influenza* |
| *Neisseria gonorrhorea* | *Serratia Marcessens* |

The crystalline material exhibited bacteriocidal activity against *S. aureus*.

The foregoing is illustrative of the present invention, and is not to be construed as limiting thereof. The invention is defined by the following claims, with equivalents of the claims to be included therein.

What is claimed is:

1. A method of treating a bacterial infection selected from the group consisting of *Staphylococcus aureus* and *Streptococcus pyogenes* comprising administering to a subject in need thereof or contacting therewith a composition consisting essentially of, uric acid, or a pharmaceutically or agriculturally acceptable salt thereof.

2. The method of claim 1, wherein the treatment of the bacterial infection is bacteriocidal or bacteriostatic.

3. The method of claim 1, wherein the composition is administered by topical, transdermal, inhalational, parenteral, oral, intraoperative, intraarticular or subcutaneous administration.

4. A method of treating a *Staphylococcus aureus* or *Streptococcus pyogenes* infection comprising administering to a subject in need thereof, an effective amount of a pharmaceutical composition consisting essentially of uric acid or a pharmaceutically acceptable salt thereof, and a pharmaceutically acceptable carrier.

5. The method of claim 1, wherein the subject is mammalian.

6. The method of claim 1, wherein the subject is human.

7. The method of claim 1, wherein the subject is a plant.

* * * * *